United States Patent [19]

Owen

[11] Patent Number: 4,720,669
[45] Date of Patent: Jan. 19, 1988

[54] GEOMEMBRANE LEAK ASSESSMENT SHELL SHAPED PROBE

[75] Inventor: Thomas E. Owen, Helotes, Tex.

[73] Assignee: Southwest Research Institute, San Antonio, Tex.

[21] Appl. No.: 849,044

[22] Filed: Apr. 7, 1986

[51] Int. Cl.[4] ............................................. G01R 31/12
[52] U.S. Cl. ..................................... 324/546; 340/605
[58] Field of Search ..................... 324/54, 52, 51, 357; 340/605

[56] References Cited

U.S. PATENT DOCUMENTS

| | | | |
|---|---|---|---|
| 3,383,863 | 5/1968 | Berry | 340/605 X |
| 4,161,689 | 7/1979 | Schlosberg et al. | 324/54 |
| 4,166,244 | 8/1979 | Woods et al. | 340/605 X |
| 4,543,525 | 9/1985 | Boryta et al. | 324/54 |

OTHER PUBLICATIONS

Shultz et al., Electrical Resistivity Technique to Assess the Integrity of Geomembrane Liners, 8-1984, pp. 1-63.

Primary Examiner—Reinhard J. Eisenzopf
Assistant Examiner—Jack B. Harvey
Attorney, Agent, or Firm—Gunn, Lee & Jackson

[57] ABSTRACT

A leak assessment shell shaped probe for determining the size of a leak in a geomembrane liner by measuring the electric current density through the liner at locations suspected to contain a leaking penetration. By comparing the observed current flow through the liner, as measured by the assessment probe, with simulated current conducting contacts, the equivalent cross-sectional area of the leak perforation may be determined.

15 Claims, 2 Drawing Figures

GEOMEMBRANE LEAK ASSESSMENT SHELL SHAPED PROBE

FIELD OF THE INVENTION

The present invention relates to an apparatus and method for determining the size and shape of a leak in a geomembrane liner. More specifically, the present invention provides an assessment probe which can be used to selectively measure the electric current and the current path through a leak in a geomembrane liner without the necessity of draining the impoundment or exposing the suspected leak area for visual inspection.

BACKGROUND

Geomembrane liners (often called flexible membrane liners) are large sheets of plastic or rubber material used as a barrier to contain liquids in an impoundment. Facilities where these liners are commonly used include hazardous waste impoundments, potable water reservoirs and other surface impoundments.

At certain types of facilities, such as hazardous waste surface impoundments, it is extremely important to know whether the liner is intact and is performing its intended containment function. Failure to detect and repair a leak can lead to serious ground water and surface water contamination.

Geomembrane liners are generally inspected for physical integrity during installation. Such inspection usually consists of a visual inspection of the surface of the individual sheets which are attached to form the liner combined with physical testing of the seams between the various sheets.

A commonly used approach for monitoring the performance of liners after they are put into service has typically been based on ground water sampling using one or more monitoring wells placed at appropriately selected locations around the impoundment. However, this ground water sampling method provides only an indirect indication of leakage and is not timely, since the ground water contamination may not be detected in monitoring wells for some time after a leak in the liner has occurred. By the time a leak has been detected by this method, substantial ground water contamination may have already occurred.

Another source of inadequacy in the ground water sampling method stems from the need to have the monitoring well in the particular aquifer which is transporting the contaminants. An adequate ground water monitoring program, therefore, requires a large number of monitoring wells along the perimeter of the impoundment with a sufficient number of wells sampling water from different levels within the various aquifers under the impoundment. Even the most elaborate ground water monitoring system, however, cannot provide monitoring as accurate as the invention system because of the inherent limitations discussed above.

The method for detecting and locating leaks in geomembrane liner systems uses an electrical measurement technique which takes advantage of the high electrical insulating properties of the liner with respect to the liquid contained above the liner and the soil under the liner. In general, geomembrane liners made from an impervious plastic material or rubber have a very high electrical resistance. A liner installed in a liquid impoundment, therefore, effectively acts as an electrical insulator between the materials contained within the liner and the surrounding environment. If the integrity of the liner is lost due to a puncture or seam separation, however, conductive liquid may then flow through the leak, thus establishing an electrical path through the liner between the contained liquid and the conductive earth in surrounding contact with the underside of the liner. The low resistance path forms an electrically detectable region corresponding to the location of a leak which may be detected and located.

The electrical measurement technique described above is discussed in greater detail in the publication "Electrical Resistivity Technique to Assess the Integrity of Geomembrane Liners," Final Technical Report, Southwest Research Institute, Project No. 14-6289, EPA Contract No. 68-03-3033 (1984), which by this reference is incorporated for all purposes.

SUMMARY OF THE INVENTION

The leak assessment probe of the present invention can be used to determine the size and shape of a leak in a geomembrane liner by measuring the electric current density through the liner at localized positions suspected to contain a leaking penetration. By comparing the observed current flow through the liner, as measured by this assessment probe, with simulated current conducting contacts consisting of different size metallic coupons placed in the liquid impoundment and connected to the external earth by insulated wires, the equivalent cross-sectional area of the leak perforation may be determined. Further, by moving the assessment probe over the suspected leak area and/or by using probe configurations of different sizes and shapes, the location and shape of the leak perforation and its distributed equivalent cross-sectional leak area may be determined and mapped.

The preferred embodiment of the invention comprises a generally hemispherical shell having inner and outer surfaces and a lower circumferential rim. The shell is adapted to contain a portion of liquid immediately adjacent to the location of a suspected leak in an impoundment. First and second electrodes are connected to the inner and outer surfaces, respectively, of the shell. Means are provided for measuring the flow of current between the two electrodes and for correlating the magnitude of the current with the size of the leak in the liner.

DETAILED DESCRIPTION OF THE PREFERRED EMBODIMENT

Figure 1:
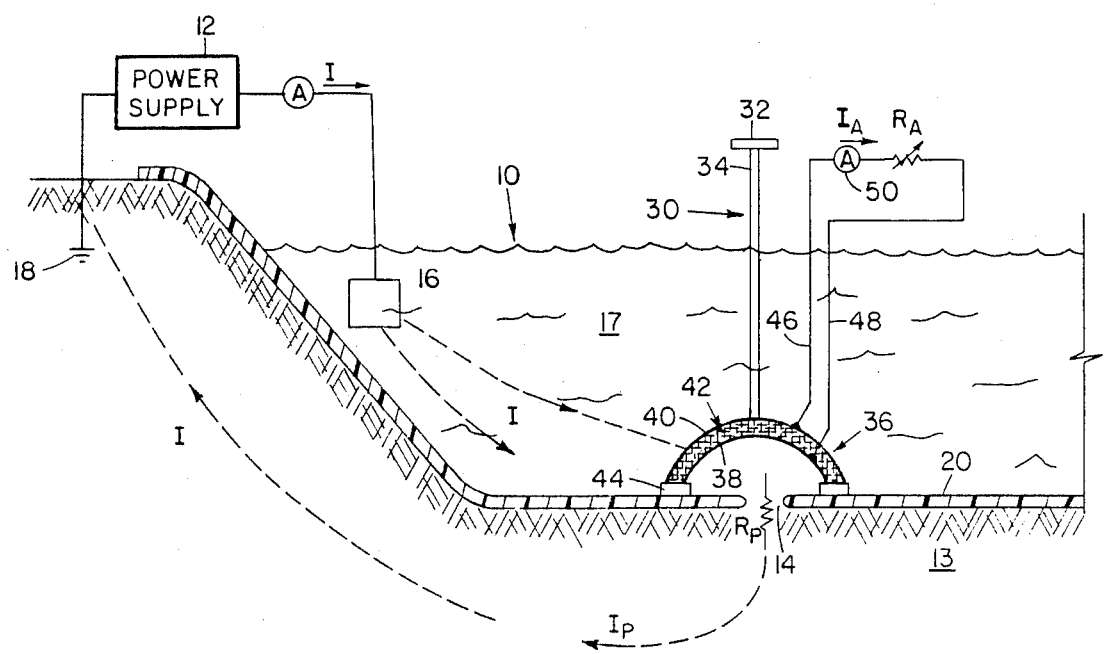
FIG. 1 is a sectional side view of a surface impoundment showing the leak assessment probe of the present invention positioned over a leak in a geomembrane liner.

The geomembrane leak assessment probe for utilizing the electrical measurement technique to determine the size and shape of leaks in a geomembrane liner is shown generally in FIG. 1. In the preferred embodiment, a voltage source 12 having a source electrode 16 and a sink electrode 18 is connected to the impoundment 10 with the source electrode 16 immersed in the conducting liquid 17 contained within the surface impoundment 10, while the sink electrode 18 is placed in the conducting earth at some point along the perimeter of the impoundment 10.

The total current I passing through the system is a function of the voltage generated by the voltage source or power supply 12 and the total resistance provided by the combined effective resistance of the contained liquid 17, the geomembrane liner 20, the conducting earth 13 in surrounding contact with the liner 20, and the contact resistances of the source and sink electrodes, 16 and 18, respectively.

The source electrode 16 of the preferred embodiment is comprised of a suitable current source electrode, such as a 3 foot diameter brass disk having a 1/16 inch thickness. Brass is particularly well suited as a source electrode material for the invention apparatus because it has excellent conductive properties and is resistant to corrosion. Other materials may also be suitable, depending on the corrosive nature of the liquid. The circular shape of the source electrode 16 helps to reduce the voltage gradient anomalies in the immediate vicinity of the electrode.

The sink electrode 18 completes the current path to the voltage source 12. The sink electrode 18 is a suitable grounding electrode, such as a copper-clad steel rod which is driven into the ground to a depth of approximately 36 inches. Increased surface area of the sink electrode 18 can be achieved by connecting three rods of the type described above with a common conductor. The increased surface area of the multiple electrode arrangement reduces the voltage drop between the electrodes and the earth resulting from the electrode contact resistance.

The geomembrane liner 20 is constructed of an impervious plastic or rubber material having a very high electrical resistance. Typical materials used to form the liner include high density polyethylene or polyvinyl chloride. The resistivity of the liner materials used in the preferred embodiment may range from approximately $2 \times 10^{14}$ ohm-cm to $2 \times 10^{16}$ ohm-cm.

The liner 20 of the preferred embodiment is formed from a plurality of elongated sheets of the resistive material, with complementary edges of the sheets attached to form an integral liner 20. The liner 20 constructed as described above is inspected visually during installation to identify punctures in the surfaces of the individual sheet members or faults in the seams between the respective sheets.

Figure 2:
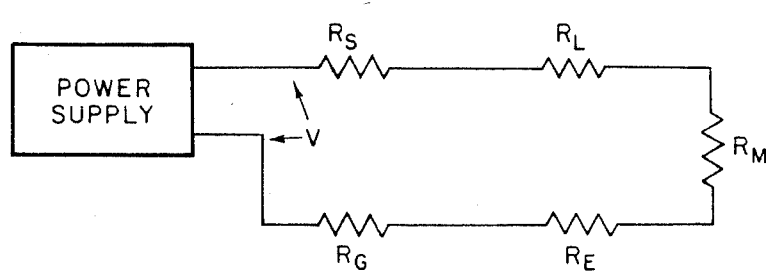
FIG. 2 is a schematic representation of the equivalent resistances of the various components of a geomembrane-lined liquid impoundment.

An unfaulted liner 20 has a very high electrical resistance for the reasons discussed above and, therefore, only a very small magnitude of current will pass therethrough. With the voltage source 12 connected to the impoundment having an unfaulted liner 20, the voltage produced by the voltage source 12 is divided approximately according to the resistance of the liquid, $R_L$, the resistance of the geomembrane liner, $R_M$, the resistance of the earth, $R_E$, and the contact resistances of the source electrode 16 and sink electrode 18, $R_S$ and $R_G$, respectively. FIG. 2 is a schematic representation of the equivalent circuit formed by the combination of the above-mentioned resistances. The current flow produced by the voltage source 12 can be calculated from the relationship:

$$I = \frac{V}{R_L + R_M + R_E + R_S + R_G} \quad (1)$$

The liquid 17 contained in the impoundment forms a large distributed resistance in which the geometric distribution of current flow is dependent upon the size, shape, and depth of the body of the liquid 17 and the position of the source electrode 16 in the liquid body. This distribution of current can be characterized in large measure by the magnitude of current passing through each unit area of a closed surface surrounding the source electrode 16. Such a characterization of current is termed the current density. The total current, I, is the surface integral of the current density computed over any closed surface surrounding the source electrode 16. Thus, in the case of the geomembrane liner 20 described above, since all of the source current must flow through the liquid-liner surface interface, the total current can be specifically represented by the integral of the current density over the liner surface defined by the liquid level line boundary. Intermediate surfaces within the liquid volume and located between the source electrode 16 and the liquid-liner interface can also be used in such surface integrations to compute the total source current.

By connecting points of equal current density on each successive intermediate surface between the current source electrode 16 and the liner, flow lines of constant current density can be established, thereby mapping the distribution of electric current within the volume of liquid 17 contained by the impoundment. By physical principle, each such current flow line will follow a path of least resistance from the source electrode 16 through the liquid and through the liner 20 to the surrounding earth 13. If the liquid 17 and the liner 20 have uniform resistivities, then the spatial distribution of the current within the liquid 17 will be dependent only upon the size and shape of the liquid-liner interface and the position of the source electrode 16 within the geometry defined by that interface. In the case of an unfaulted geomembrane liner, the resistance contrast between the high resistivity liner and the more conductive liquid 17 will be such that the current density through the liquid-liner surface and through the various intermediate surfaces located well away from the source electrode 16 will be relatively uniform.

The finite resistivity of the liquid 17 contained within the liner 20 causes a voltage drop between the surface of the source electrode 16 and the liner 20 when the source power supply 12 is energized. This voltage drop, $V_L$, is expressed by:

$$V_L = IR_L = \left( \frac{R_L}{R_L + R_M + R_E + R_S + R_G} \right) V. \quad (2)$$

Because the resistance of the liquid body 17, $R_L$, is a distributed resistance, there are also voltage differences within the body of the liquid 17. In particular, along each line of constant current density there are incremental voltage drops whose sums can be considered to be approximately equal to the total voltage drop, $V_L$, in the liquid 17. By connecting points of equal potential along each line of constant density, specific surfaces, termed equipotential surfaces, are identified and the vector directions normal to such equipotential surfaces (parallel to the current density flow direction at each point on the surface) define the direction of the potential gradient within the body of the liquid. Such equipotential surfaces and potential gradients are important since, by their measurement and interpretation, anomalous conditions of current density distribution within the impounded liquid 17 can be measured and interpreted to reveal the presence and location of the leak 14 in the liner 20.

When the current density within the contained liquid 17 is relatively uniform, as in the case of an unfaulted liner 20, the voltage gradients in the body of the liquid 17 are small. When a leak 14 is present in the liner 20, the current flow through the liner 20 tends to concentrate along the lower resistance path through the leak 14, thereby causing higher voltage gradients in the vicinity of the leak 14. These anomalous changes in the potential gradients also change the spatial location and shapes of the equipotential surfaces mentioned above.

FIG. 1 illustrates a generalized physical embodiment of the invention geomembrane leak assessment probe 30 for utilizing the principles discussed above to determine the size and shape of a leak in a geomembrane liner. As shown in FIG. 1, the probe 30 consists of an appropriate handle 32 and a vertical shaft or staff 34 attached to a hemispherical shell 36. The hemispherical shell 36 is comprised of an electrically insulating material 42, such as either a flexible or a rigid rubber or plastic material, with conducting electrodes 38 and 40 on its inner and outer surfaces, respectively. The two electrodes are physically and electrically separated by the shell material 42, which may have any practical thickness. The surface area and geometrical contours of the two electrodes are not necessarily required to conform to the area or contour of the hemispherical shell 32. However, they must have a surface area and an electrical conductivity which, in electrical combination, is very much greater than that of the dimensional cross-section and conductivity of the leak penetration 14 enclosed by the lower rim 44 of the shell 36.

A circuit between the two electrodes is formed by insulated wires 46 and 48 which are connected to a current measuring meter 50 or other current measuring circuitry at the surface of the impoundment. The current flowing between the electrodes 38 and 40 is equal to the total current flowing through the area of the liner enclosed by the lower rim 44 of the hemispherical shell 36, provided that the lower rim 44 of the shell is in close contact with the liner 20 at all points around its perimeter. If such close contact is not made, liquid current-carrying paths will exist under the lower rim 44 of the shell such that the current measured by the electrodes will be somewhat less than the total current flow through the liner area enclosed by the shell 36. Therefore, in this case, the resulting equivalent size of the leak area derived from the electrode-measured current will be smaller than the actual leak area.

In operation, the geomembrane leak assessment probe 30 is placed against the liner 20, first making sure that the hemispherical shell 36 does not entrap any substantial amount of air but is essentially filled with liquid. The position(s) of placement on the liner 20 will, in general, correspond to previously located areas suspected of having a leak penetration through the liner. The shell 36 is then pressed downward against the liner 20 to effect a close contact or seal between the lower rim 44 of the shell 36 and the liner 20 via the hand-held staff 34 or other means attached to the top of the shell 36. A leak-scaling resistance, $R_A$, in the current measurement circuit is then adjusted to cause the observed current to be reduced to one-half the current flow observed when $R_A = 0$. Under this condition, the resistance, $R_A$, is equal to the resistance of the combined leak and liner resistance, $R_P$, enclosed by the perimeter 44 of the shell 36.

The values of $R_A$ obtained in the various leak assessment measurements may be separately calibrated in terms of the equivalent contact area and electrical resistance of several leak-simulating metallic coupons of different sizes placed in contact with the impounded liquid.

An alternative arrangement for establishing the equivalent size of the cross-sectional area of the leak enclosed by the shell 36 is one in which either the inner or outer electrode on the hemispherical shell 36 is subdivided into a plurality of graduated sectors whose contact area with the liquid 17 ranges from the smallest to the largest expected equivalent area of the leak to be measured. Then, by means of separate insulated wires leading from the various sizes of these electrode sectors and a switching arrangement, the current observed with the largest electrode (or with all electrode sectors connected together) is then reduced to one half this value by selectively switching to an electrode (or combination of electrodes) of smaller area. The area of the electrode(s) selected by this switching process is then equal to the equivalent leak area.

Although the invention method has been described in connection with the preferred embodiment, it is not intended to limit the invention to the particular form set forth, but on the contrary, it is intended to cover such alternatives, modifications, and equivalents as may be included within the spirit and scope of the invention as defined by the appended claims.

I claim:

1. An apparatus for determining the size of a leak in a liner, said liner having one face in contact with a conductive liquid contained by said liner and having the opposite face in contact with a conducting material, comprising:

means for producing a voltage drop between said contained liquid and said conducting material, thereby creating a flow of current through said liquid and said liner;

means defining a shell having an inner surface, an outer surface and a lower circumferential rim, said shell being adapted to contain a portion of said liquid adjacent to a leak in said liner with said lower rim in contact with said liner;

a first electrode on said inner surface of said shell, said first electrode in contact with said portion of said liquid contained within said shell;

a second electrode on said outer surface of said shell, said second electrode in contact with a portion of said liquid adjacent to said outer surface of said shell;

means for electrically isolating said first electrode from said second electrode;

means for measuring the flow of current from said first electrode to said second electrode; and means for correlating said flow of current with the size of said leak.

2. The apparatus according to claim 1, further comprising means for urging said shell into contact with said liner such that said lower rim of said shell forms a seal between said portion of said liquid contained within said shell and the other portion of said liquid contained by said liner.

3. The apparatus according to claim 2, said means for urging said shell into contact with said liner comprising a shaft having first and second ends, said first end being attached to said shell, said second end having a handle attached thereto.

4. The apparatus according to claim 1, said shell being generally hemispherical and being formed from an electrically insulating material.

5. The apparatus according to claim 1, said means for measuring said flow of current comprising an ammeter in series with said first and second electrodes.

6. The apparatus according to claim 5, said means for correlating said flow of current with the size of said leak comprising a leak scaling resistance in series with said ammeter and said first and second electrodes.

7. An apparatus for determining the size of a leak in a liner, said liner having one face in contact with a conductive liquid contained by said liner and having the opposite face in contact with a conducting material, comprising:
   means for producing a voltage drop between said contained liquid and said conducting material, thereby creating a flow of current through said liquid and said liner;
   means defining a shell having an inner surface, an outer surface and a lower circumferential rim, said shell being adapted to contain a portion of said liquid adjacent to a leak in said liner with said lower rim in contact with said liner;
   a first electrode means on said inner surface of said shell, said first electrode means being in contact with said portion of said liquid contained within said shell, said first electrode means comprising a plurality of electrode sectors having graduated surface areas, said electrode sectors being electrically connectable in a plurality of configurations to define a plurality of contact resistances between said first electrode means and said portion of said liquid contained within said shell;
   a second electrode means on said outer surface of said shell, said second electrode means being in contact with a portion of said liquid adjacent to said outer surface of said shell;
   means for electrically isolating said first electrode means from said second electrode means;
   means for measuring the flow of current from said first electrode means to said second electrode means; and
   means for correlating said flow of current with the size of said leak.

8. The apparatus according to claim 7, further comprising means for urging said shell into contact with said liner such that said lower rim of said shell forms a seal between said portion of said liquid contained within said shell and the other portion of said liquid contained by said liner.

9. The apparatus according to claim 8, said means for urging said shell into contact with said liner comprising a shaft having first and second ends, said first end being attached to said shell, said second end having a handle attached thereto.

10. The apparatus according to claim 7, said shell being generally hemispherical and being formed from an electrically insulating material.

11. The apparatus according to claim 7, said means for measuring said flow of current comprising an ammeter in series with said first and second electrode means.

12. The apparatus according to claim 11, said means for correlating said flow of current with the size of said leak comprising an electrical switching means for electrically connecting said sectors comprising said first electrode means in a plurality of configurations to change the effective contact resistance between said first electrode means and said portion of said liquid contained within said shell, said contact resistance being correlatable with the size of said leak.

13. A method of determining the size of a leak in a liner, said liner having one face in contact with a conductive liquid contained by said liner and having the opposite face in contact with a conducting material, comprising the steps of:
   producing a voltage drop between said contained liquid and said conducting material, thereby creating a flow of current through said liquid and said liner;
   placing a current measuring means in surrounding relationship to a portion of said liquid immediately adjacent to a leak in said liner;
   said current measuring means comprising:
      a shell having an inner surface, an outer surface and a lower circumferential rim, said shell being adapted to contain said portion of said liquid adjacent to said leak in said liner with said lower rim in contact with said liner;
      a first electrode on said inner surface of said shell, said first electrode in contact with said portion of said liquid contained within said shell;
      a second electrode on said outer surface of said shell, said electrode in contact with the portion of said liquid adjacent to said outer surface of said shell; and
      means for electrically isolating said first electrode from said second electrode;
   measuring the flow of current in said portion of said liquid immediately adjacent to said leak in said liner; and
   correlating said flow of current with the size of said leak in said liner.

14. The method according to claim 13, said step of measuring said flow of current further comprising the step of observing said flow of current as a readout on an ammeter, said ammeter being in series connection with said first and second electrodes.

15. The method according to claim 14, said step of correlating said flow of electric current with the size of said leak further comprising the steps of:
   connecting a variable leak scaling resistance in series with said ammeter and said first and second electrodes;
   observing a first magnitude of said current corresponding to said leak scaling resistance having a value of zero;
   increasing the value of said leak scaling resistance until said magnitude of said current flow is equal to one-half of said first magnitude;
   observing the value of said leak scaling resistance corresponding to said magnitude of said current flow being equal to one-half of said first magnitude; and
   correlating the observed value of said leak scaling resistance with the size of said leak.

* * * * *